United States Patent
Lalezari et al.

(10) Patent No.: US 9,040,553 B2
(45) Date of Patent: May 26, 2015

(54) PHENOXYISOBUTYRIC ACID COMPOUNDS AND METHOD OF SYNTHESIS

(71) Applicants: Iraj Lalezari, Louisville, CO (US); Jill Fabricant, Corona Del Mar, CA (US)

(72) Inventors: Iraj Lalezari, Louisville, CO (US); Jill Fabricant, Corona Del Mar, CA (US)

(73) Assignee: CELL VIABLE CORPORATION, Corona del Mar, CA (US)

( * ) Notice: Subject to any disclaimer, the term of this patent is extended or adjusted under 35 U.S.C. 154(b) by 0 days.

(21) Appl. No.: 13/940,008

(22) Filed: Jul. 11, 2013

(65) Prior Publication Data

US 2014/0350045 A1 Nov. 27, 2014

Related U.S. Application Data

(63) Continuation of application No. 13/199,941, filed on Sep. 13, 2011, now abandoned.

(60) Provisional application No. 61/403,534, filed on Sep. 17, 2010.

(51) Int. Cl.
| | |
|---|---|
| *C07D 307/87* | (2006.01) |
| *C07D 215/14* | (2006.01) |
| *C07D 215/52* | (2006.01) |
| *C07C 235/72* | (2006.01) |
| *C07D 215/50* | (2006.01) |
| *C07D 219/04* | (2006.01) |
| *C07C 275/42* | (2006.01) |
| *C07C 229/40* | (2006.01) |
| *A61K 8/41* | (2006.01) |
| *A61K 8/42* | (2006.01) |
| *A61K 8/49* | (2006.01) |
| *A61Q 19/08* | (2006.01) |
| *C07C 215/76* | (2006.01) |
| *C07C 233/75* | (2006.01) |
| *C07C 235/74* | (2006.01) |
| *C07C 275/34* | (2006.01) |
| *C07D 215/12* | (2006.01) |

(52) U.S. Cl.
CPC .............. *C07D 307/87* (2013.01); *A61K 8/411* (2013.01); *A61K 8/42* (2013.01); *A61K 8/4926* (2013.01); *A61Q 19/08* (2013.01); *C07C 215/76* (2013.01); *C07C 233/75* (2013.01); *C07C 235/74* (2013.01); *C07C 275/34* (2013.01); *C07D 215/12* (2013.01); *C07D 215/50* (2013.01); *C07D 215/52* (2013.01); *C07D 219/04* (2013.01); *C07C 229/40* (2013.01); *C07C 235/72* (2013.01); *C07C 275/42* (2013.01); *C07D 215/14* (2013.01)

(58) Field of Classification Search
None
See application file for complete search history.

(56) References Cited

U.S. PATENT DOCUMENTS

| 6,605,642 B2* | 8/2003 | Rahbar et al. ............... 514/563 |
| 7,030,133 B2* | 4/2006 | Rahbar et al. ............... 514/297 |
| 2012/0071502 A1* | 3/2012 | Lalezari et al. ............. 514/297 |

* cited by examiner

*Primary Examiner* — Timothy R Rozof
(74) *Attorney, Agent, or Firm* — Hedman & Costigan, P.C.; James V. Costigan; Kathleen A. Costigan

(57) ABSTRACT

The present invention provides a process for the synthesis of substituted phenoxymethylpropionic acid and related compounds. The compounds are useful for inhibiting the formation of AGEs (Advanced Glycation End Products).

5 Claims, No Drawings

PHENOXYISOBUTYRIC ACID COMPOUNDS AND METHOD OF SYNTHESIS

BACKGROUND OF THE INVENTION

The present invention relates generally to the synthesis and production of novel substituted arylureidophenoxymethylpropionic acids that are useful in pharmaceutical applications. One use of the disclosed compounds is as anti AGE (Advanced Glycation Products) compound for the treatment of diabetes.

It is known in the art that elevated concentration of reducing sugars in the blood and in the intracellular environment results in the nonenzymatic formation of glycation and dehydration condensation complexes known as advanced glycation end-products or aminaglycation end products (AGEs). Nonenzymatic glycation is a complex series of reactions between reducing sugars and amino groups of proteins, lipids, and DNA. These complex products form on free amino groups on proteins, on lipids and on DNA (Bucala and Cerami, 1992; Bucala et al., 1993; Bucala et al., 1984). This phenomenon is called "browning" or a "Maillard" reaction and was discovered early in the last century by the food industry (Maillard, 1916). The reaction is initiated with the reversible formation of Schiffs base which undergoes rearrangement to form a stable Amadori product. Both Schiffs base and Amadori product further undergo a series of reactions through dicarbonyl intermediates to form AGEs. The significance of a similar process in biology became evident only after the discovery of the glycosylated hemoglobins and their increased presence in diabetic patients (Rahbar, 1968; Rahbar et al., 1969). In human diabetic patients and in animal models of diabetes, these nonenzymatic reactions are accelerated and cause increased AGE formation and increased glycation of long-lived proteins such as collagen, fibronectin, tubulin, lens crystallin, myelin, laminin and actin, in addition to hemoglobin and albumin, and also of LDL associated lipids and apoprotein. Moreover, brown pigments with spectral and fluorescent properties similar to those of late-stage Maillard products have also been found in vivo in association with several long-lived proteins such as crystalline lens proteins and collagen from aged individuals. An age-related linear increase in pigments was observed in human dura collagen between the ages of 20 to 90 years. AGE modified proteins increase slowly with aging and are thought to contribute to normal tissue remodeling. Their level increases markedly in diabetic patients as a result of sustained high blood sugar levels and lead to tissue damage through a variety of mechanisms including alteration of tissue protein structure and function, stimulation of cellular responses through AGE specific receptors or the generation of reactive oxygen species (ROS) (for a recent review see Boel et al., 1995). The structural and functional integrity of the affected molecules, which often have major roles in cellular functions, become disturbed by these modifications, with severe consequences on affected organs such as kidney, eye, nerve, and micro-vascular functions (Silbiger et al., 1993; Brownlee et al., 1985).

Structural changes on macromolecules by AGEs are known to accumulate under normal circumstances with increasing age. This accumulation is severely accelerated by diabetes and is strongly associated with hyperglycemia. For example, formation of AGE on protein in the subendothelial basement membrane causes extensive cross-link formation which leads to severe structural and functional changes in protein/protein and protein/cell interaction in the vascular wall (Haitoglou et al., 1992; Airaksinen et al., 1993).

Enhanced formation and accumulation of advanced glycation end products (AGEs) have been implicated as a major pathogenesis process leading to diabetic complications, normal aging, atherosclerosis and Alzheimer's disease. This process is accelerated by diabetes and has been postulated to contribute to the development of a range of diabetic complications including nephropathy (Nicholls and Mandel, 1989), retinopathy (Hammes et al., 1991) and neuropathy (Cameron et al., 1992). Particularly, tissue damage to the kidney by AGEs leads to progressive decline in renal function, end-stage renal disease (ESRD) (Makita et al., 1994), and accumulation of low-molecular-weight (LMW) AGE peptides (glycotoxins) (Koschinsky et al., 1997) in the serum of patients with ESRD (Makita et al., 1991). These low molecular weight (LMW)-AGEs can readily form new crosslinks with plasma or tissue components, e.g., low density lipoprotein (LDL) (Bucala et al., 1994) or collagen (Miyata et al., 1993) and accelerate the progression of tissue damage and morbidity in diabetics.

Direct evidence indicating the contribution of AGEs in the progression of diabetic complications in different lesions of the kidneys, the rat lens and in atherosclerosis has been reported (Vlassara et al., 1994; Vlassara et al., 1995; Horie et al., 1997; Matsumoto et al., 1997; Soulis-Liparota et al., 1991; Bucala and Vlassara, 1997; Bucala and Rahbar, 1998; Park et al., 1998). Indeed, the infusion of pre-formed AGEs into healthy rats induces glomerular hypertrophy and mesangial sclerosis, gene expression of matrix proteins and production of growth factors (Brownlee et al., 1991; Vlassara et al., 1995). Several lines of evidence indicate that the increase in reactive carbonyl intermediates (methylglyoxal, glycolaldehyde, glyoxal, 3-deoxyglucosone, malondialdehyde and hydroxynonenal) is the consequence of hyperglycemia in diabetes. "Carbonyl stress" leads to increased modification of proteins and lipids, followed by oxidant stress and tissue damage (Baynes and Thorpe, 1999; Onorato et al., 1998; McLellan et al., 1994). Further studies have revealed that aminoguanidine (AG), an inhibitor of AGE formation, ameliorates tissue impairment of glomeruli and reduces albuminuria in induced diabetic rats (Soulis-Liparota et al., 1991; Itakura et al., 1991). In humans, decreased levels of hemoglobin (Hb)-AGE (Makita et al., 1992) concomitant with amelioration of kidney function as the result of aminoguanidine therapy in diabetic patients, provides more evidence for the importance of AGEs in the pathogenesis of diabetic complications (Bucala and Vlassara, 1997).

The global prevalence of diabetes mellitus, in particular in the United States, afflicting millions of individuals with significant increases of morbidity and mortality, together with the great financial burden for the treatment of diabetic complications in this country, are major incentives to search for and develop drugs with a potential for preventing or treating complications of the disease. So far the mechanisms of hyperglycemia-induced tissue damage in diabetes are not well understood. However, four pathogenic mechanisms have been proposed, including increased polyol pathway activity, activation of specific protein kinase C (PKC) isoforms, formation and accumulation of advanced glycation endproducts, and increased generation of reactive oxygen species (ROS) (Kennedy and Lyons, 1997). Most recent immunohistochemical studies on different tissues from kidneys obtained from ESRD patients (Hone et al., 1997) and diabetic rat lenses (Matsumoto et al., 1997), by using specific antibodies against carboxymethyllysine (CML), pentosidine, the two known glycoxidation products and pyrraline, have localized these AGE components in different lesions of the kidneys and the rat lens, and have provided more evidence in favor of protein- AGE formation in close association with generation of ROS to be major factors in causing permanent and irreversible modification of tissue proteins. Therefore, inhibitors of AGE formation and antioxidants hold promise as effective means of prevention and treatment of diabetic complications.

The Diabetic Control and Complications Trial (DCCT), has identified hyperglycemia as the main risk factor for the development of diabetic complications (The Diabetes Control and Complications Trial Research Group, 1993). Compelling evidence identifies the formation of advanced glycation endproducts as the major pathogenic link between hyperglycemia and the long-term complications of diabetes (Makita et al., 1994; Koschinsky et al., 1997; Makita et al., 1993; Bucala et al., 1994; Bailey et al., 1998).

The reactions between reducing sugars and amino groups of proteins, lipids and DNA undergo a series of reactions through dicarbonyl intermediates to generate advanced glycation endproducts (Bucala and Cerami, 1992; Bucala et al., 1993; Bucala et al., 1984).

In human diabetic patients and in animal models of diabetes, AGE formation and accumulation of long-lived structural proteins and lipoproteins have been reported. Most recent reports indicate that glycation inactivates metabolic enzymes (Yan and Harding, 1999; Kato et al., 2000; Verbeke et al., 2000; O'Harte et al., 2000). The glycation-induced change of immunoglobin G is of particular interest. Reports of glycation of the Fab fragment of IgG in diabetic patients suggest that immune deficiency observed in these patients may be explained by this phenomenon (Lapolla et al., 2000). Furthermore, an association between IgM response to IgG damaged by glycation and disease activity in rheumatoid arthritis has been reported (Lucey et al., 2000). Also, impairment of high-density lipoprotein function by glycation has been described (Hedrick et al., 2000).

Methylglyoxal (MG) has recently received considerable attention as a common mediator and the most reactive dicarbonyl to form AGEs (Phillips and Thornalley, 1993; Beisswenger et al., 1998). It is also a source of reactive oxygen species (ROS) (free radicals) generation in the course of glycation reactions (Yim et al., 1995).

Nature has devised several humoral and cellular defense mechanisms to protect tissues from the deleterious effects of "carbonyl stress" and accumulation of AGEs, e.g., the glyoxylase systems (I and II) and aldose reductase catalyze the detoxification of MG to D-lactate (McLellan et al., 1994). Amadoriases are also a novel class of enzymes found in Aspergillus which catalyze the deglycation of Amadori products (Takahashi et al., 1997). Furthermore, several AGE-receptors have been characterized on the surface membranes of monocytes and on macrophage, endothelial, mesangial and hepatic cells. One of these receptors, RAGE, a member of the immunoglobulin superfamily, has been found to have a wide tissue distribution (Schmidt et al., 1994; Yan et al., 1997). The discovery of various natural defense mechanisms against glycation and AGE formation suggests an important role of AGEs in the pathogenesis of vascular and peripheral nerve damage in diabetes. MG binds to and irreversibly modifies arginine and lysine residues in proteins. MG modified proteins have been shown to be ligands for the AGE receptor (Westwood et al., 1997) indicating that MG modified proteins are analogous (Schalkwijk et al., 1998) to those found in AGEs. Furthermore, glycolaldehyde, a reactive intermediate in AGE formation, generates an active ligand for macrophage scavenger receptor (Nagai et al., 2000). The effects of MG on LDL have been characterized in vivo and in vitro (Bucala et al., 1993).

Lipid peroxidation of polyunsaturated fatty acids (PUFA), such as arachidonate, also yields carbonyl compounds; some are identical to those formed from carbohydrates (Al-Abed et al., 1996), such as MG and GO, and others are characteristic of lipids, such as malondialdehyde (MDA) and 4-hydroxynonenal (HNE) (Requena et al., 1997). The latter two carbonyl compounds produce lipoxidation products (Al-Abed et al., 1996; Requena et al., 1997). A recent report emphasizes the importance of lipid-derived MDA in the cross-linking of modified collagen and in diabetes mellitus (Slatter et al., 2000). A number of AGE compounds, both fluorophores and nonfluorescent, are involved in crosslinking proteins and have been characterized (Baynes and Thorpe, 1999). In addition to glucose derived AGE-protein crosslinks, AGE crosslinking also occurs between tissue proteins and AGE-containing peptide fragments formed from AGE-protein digestion and turnover. These reactive AGE-peptides, now called glycotoxins, are normally cleared by the kidneys. In diabetic patients, these glycotoxins react with the serum proteins and are a source for widespread tissue damage (He et al., 1999).

However, detailed information on the chemical nature of the crosslink structures remain unknown. The crosslinking structures characterized to date, on the basis of chemical and spectroscopic analyses, constitute only a small fraction of the AGE crosslinks which occur in vivo, with the major crosslinking structure(s) still unknown. Most recently, a novel acid-labile AGE-structure, N-omega-carboxymethylarginine (CMA), has been identified by enzymatic hydrolysis of collagen. Its concentration was found to be 100 times greater than the concentration of pentosidine (Iijima et al., 2000) and it is assumed to be a major AGE crosslinking structure.

In addition to aging and diabetes, the formation of AGEs has been linked with several other pathological conditions. IgM anti-IgG-AGE appears to be associated with clinical measurements of rheumatoid arthritis activity (Lucey et al., 2000). A correlation between AGEs and rheumatoid arthritis was also made in North American Indians (Newkirk et al., 1998). AGEs are present in brain plaques in Alzheimer's disease and the presence of AGEs may help promote the development of Alzheimer's disease (Durany et al., 1999; Munch et al., 1998; Munch et al., 1997). Uremic patients have elevated levels of serum AGEs compared to age-matched controls (Odani et al., 1999; Dawnay and Millar, 1998). AGEs have also been correlated with neurotoxicity (Kikuchi et al., 1999). AGE proteins have been associated with atherosclerosis in mice (Sano et al., 1999) and with atherosclerosis in persons undergoing hemodialysis (Takayama et al., 1998). A study in which aminoguanidine was fed to rabbits showed that increasing amounts of aminoguanidine led to reduced plaque formation in the aorta thus suggesting that advanced glycation may participate in atherogenesis and raising the possibility that inhibitors of advanced glycation may retard the process (Panagiotopoulos et al., 1998). Significant deposition of N(epsilon)-carboxymethyl lysine (CML), an advanced glycation endproduct, is seen in astrocytic hyaline inclusions in persons with familial amyotrophic lateral sclerosis but is not seen in normal control samples (Kato et al., 1999; Shibata et al., 1999). Cigarette smoking has also been linked to increased accumulation of AGEs on plasma low density lipoprotein, structural proteins in the vascular wall, and the lens proteins of the eye, with some of these effects possibly leading to pathogenesis of atherosclerosis and other diseases associated with tobacco usage (Nicholl and Bucala, 1998). Finally, a study in which aminoguanidine was fed to rats showed that the treatment protected against progressive cardiovascular and renal decline (Li et al., 1996).

The mechanism of the inhibitory effects of aminoguanidine in the cascade of glycosylation events has been investigated. To date, the exact mechanism of AG-mediated inhibition of AGE formation is not completely known. Several lines of in vitro experiments resulted in contrasting conclusions. Briefly, elevated concentrations of reducing sugars cause reactions between carbohydrate carbonyl and protein amino groups leading to: 1. Reversible formation of Schiff's bases followed by 2. Amadori condensation/dehydration products such as 3-deoxyglucason (3-DG), a highly reactive dicarbonyl compound (Kato et al., 1990). 3. Irreversible and highly reactive advanced glycosylation endproducts. Examples of early Amadori products are ketoamines which undergo further condensation reactions to form late AGEs. A number of AGE products have been purified and characterized recently, each one constituting only minor fractions of the in vivo generated AGEs. Examples are pyrraline, pentosidine, carboxymethyl-lysine (CML), carboxyethyl-lysine (CEL), crossline, pyrrolopyridinium, methylglyoxal lysine dimer (MOLD), Arg-Lys imidazole, arginine pyridinium, cypentodine, piperidinedinone enol and alkyl, formyl, diglycosylpyrrole (Vlassara, 1994).

Analysis of glycation products formed in vitro on a synthetic peptide has demonstrated that aminoguanidine does not inhibit formation of early Amadori products (Edelstein and Brownlee, 1992). Similar conclusions were reached by analysis of glycation products formed on BSA (Requena et al., 1993). In both experiments AGE formation was strongly inhibited by AG as analyzed by fluorescence measurements and by mass spectral analysis. The mass spectral analysis did not detect peptide complexes with molecular mass corresponding to an incorporation of AG in the complex. Detailed mechanistic studies using NMR, mass spectroscopy and X-ray diffraction have shown that aminoguanidine reacts with AGE precursor 3-DG to form 3-amino-5- and 3-amino-6-substituted triazines (Hirsch et al., 1992). In contrast, other experiments using labeled .sup.14C-AG with lens proteins suggest that AG becomes bound to the proteins and also reacts with the active aldose form of free sugars (Harding, 1990).

Several other potential drug candidates as AGE inhibitors have been reported. These studies evaluated the agent's ability to inhibit AGE formation and AGE-protein crosslinking compared to that of aminoguanidine (AG) through in vitro and in vivo evaluations (Nakamura et al., 1997; Kochakian et al., 1996). A recent breakthrough in this field is the discovery of a compound, N-phenacylthiazolium bromide (PTB), which selectively cleaves AGE-derived protein crosslinks in vitro and in vivo (Vasan et al., 1996; Ulrich and Zhang, 1997). The pharmacological ability to break irreversible AGE-mediated protein crosslinking offers potential therapeutic use.

It is well documented that early pharmaceutical intervention against the long-term consequences of hyperglycemia-induced crosslinking prevent the development of severe late complications of diabetes. The development of nontoxic and highly effective drugs that completely stop glucose-mediated crosslinking in the tissues and body fluids is a highly desirable goal. The prototype of the pharmaceutical compounds investigated both in vitro and in vivo to intervene with the formation of AGEs on proteins is aminoguanidine (AG), a small hydrazine-like compound (Brownlee et al., 1986). However, a number of other compounds were found to have such an inhibitory effect on AGE formation. Examples are D-lysine. (Sensi et al., 1993), desferrioxamine (Takagi et al., 1995), D-penicillamine (McPherson et al., 1988), thiamine pyrophosphate and pyridoxamine (Booth et al., 1997) which have no structural similarities to aminoguanidme.

Clinical trials of AG as the first drug candidate intended to inhibit AGE formation are in progress (Corbett et al., 1992). A number of hydrazine-like and non-hydrazine compounds have been investigated. So far AG has been found to be the most useful with fewer side effects than other tested compounds of the prior art. AG is also a well known selective inhibitor of nitric oxide (NO) and can also have antioxidant effects (Tilton et al., 1993).

A number of other potential drug candidates to be used as AGE inhibitors have been discovered recently and evaluated both in vitro and in vivo (Nakamura et al., 1997; Soulis et al., 1997). While the success in studies with aminoguanidine and similar compounds is promising, the need to develop additional inhibitors of AGEs continues to exist in order to broaden the availability and the scope of this activity and therapeutic utility.

SUMMARY OF THE INVENTION

The compounds of the present invention have the following formulas:

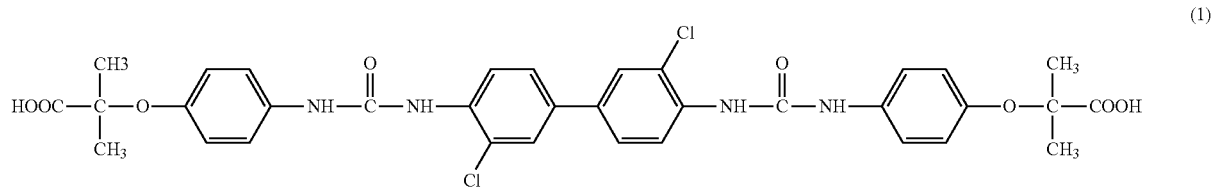

(1)

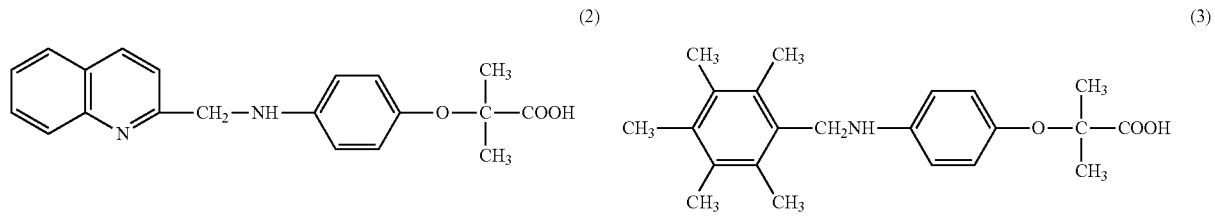

(2) (3)

-continued
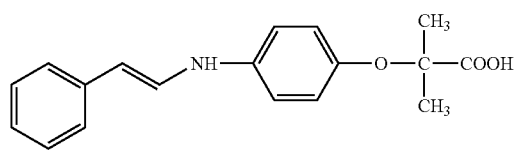 (4)
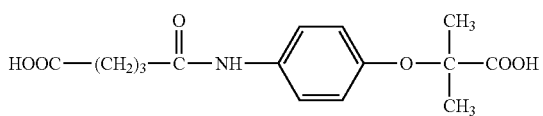 (5)
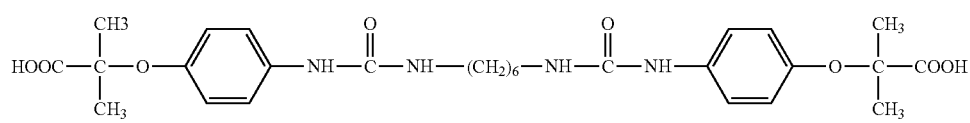 (6)
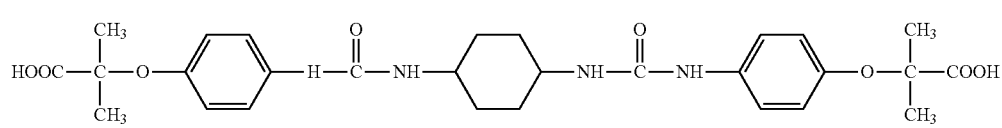 (7)
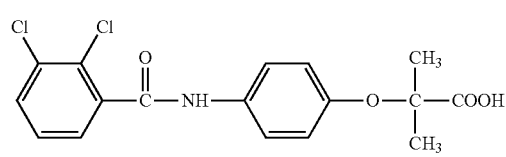 (8)
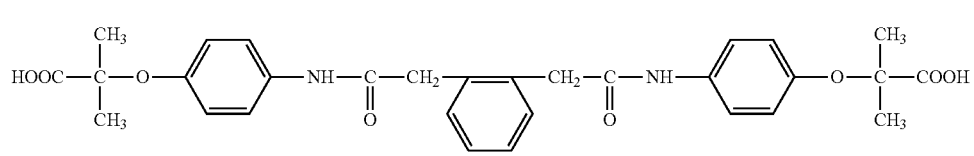 (9)
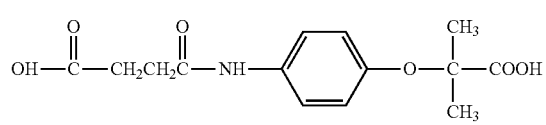 (10)
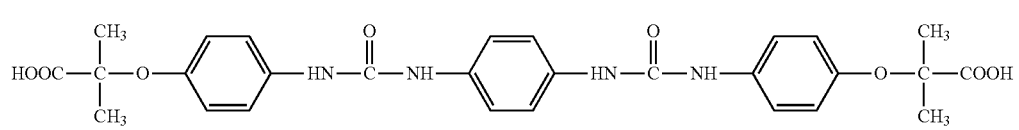 (11)
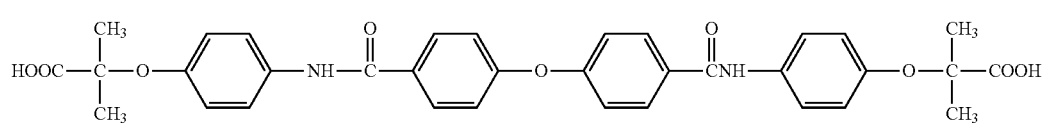 (12)
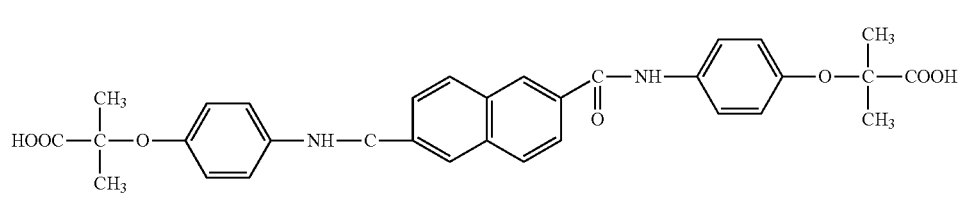 (13)
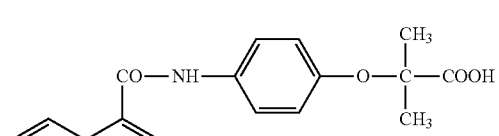 (14)
 (15)

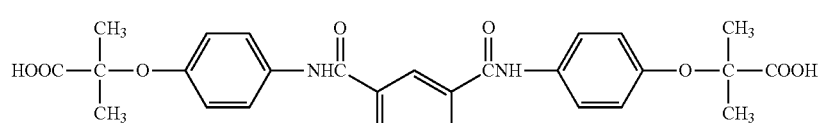
(16)

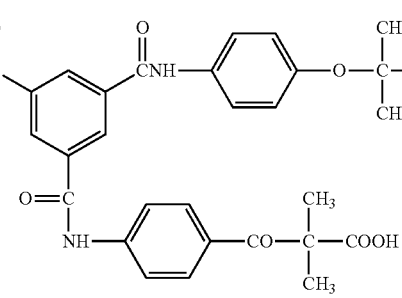

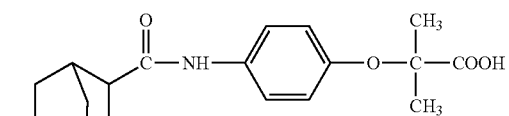
(17)

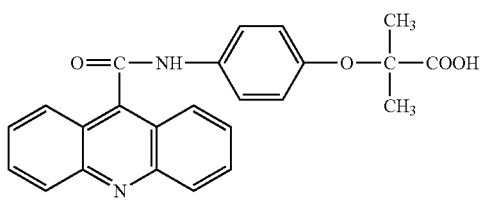
(18)

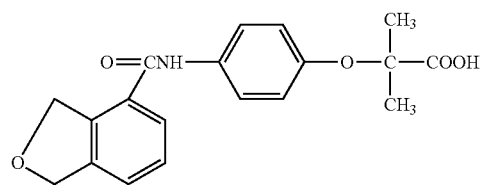
(19)

DETAILED DESCRIPTION OF THE INVENTION

The present inventor has previously reported new classes of compounds which are aryl (and heterocyclic) ureido and aryl (and heterocyclic) carboxamido phenoxyisobutyric acids and also benzoic acid derivatives and related compounds as inhibitors of glycation and AGE formation (Rahbar et al., 1999; Rahbar et al., 2000; Rahbar et al., 2002). See also U.S. Pat. Nos. 5,093,367; 6,072,072; 6,337,350; 6,005,642 and 7,030133 which are incorporated herein by reference. An elevated concentration of reducing sugars (i.e., glucose) in the blood and in the intracellular environment of an animal, namely a human, typically results in the nonenzymatic formation of glycation and dehydration condensation complexes known as advanced glycation end-products (AGE). These AGE complex products form on free amino groups, on proteins, on lipids and on DNA (Bucala and Cerami, Adv Pharmacol 23:1-34, 1992; Bucala et al., Proc Natl Acad Sci 90:6434-6438, 1993; Bucala et al., Proc Natl. Acad Sci 81:105-109, 1984). This phenomenon is called "browning" or a "Maillard" reaction and was discovered in the last century by the food industry (Maillard, Ann Chim 5:258-317, 1916). The significance of a similar process in biology became evident only after the discovery of the glycosylated hemoglobins and their increased presence in diabetic patients (Rahbar, Clin Chim Acta 20:381-5, 1968; Rahbar et al., Biochem Biophys Res Commun 36:838-43, 1969). A diabetic patient's AGE level increases markedly as a result of sustained high blood sugar levels and often leads to tissue damage through a variety of mechanisms including alteration of tissue protein structure and function, stimulation of cellular responses through AGE specific receptors and/or the generation of reactive oxygen species (ROS) (for a recent review see Boel et al., J Diabetes Complications 9:104-29, 1995). These AGE have been shown to cause complications in patients suffering from various pathological conditions, including, but not limited to, diabetes mellitus, rheumatoid arthritis, Alzheimer's Disease, uremia and in atherosclerosis in persons undergoing hemodialysis.

Advanced glycation end-products bind to cell surface receptors on a variety of cells including, but not limited to, endothelial cells of the microvasculature, monocytes and macrophages, smooth muscle cells, mesangial cells and neurons through a specific receptor for AGEs, termed RAGE. RAGE is a member of the immunoglobulin super family of cell surface molecules. Increased levels of RAGE are expressed in a number of tissues including, but not limited to, aging tissues, diabetic tissues, the vasculature and the kidney. Activation of RAGE has been implicated in a variety of conditions including, but not limited to, acute and chronic inflammation, in certain complications of diabetes, nephropathy, atherosclerosis and retinopathy, Alzheimer's disease, erectile dysfunction and in tumor invasion and metastases.

The complications associated with each of these aforementioned pathological conditions places a significant burden on afflicted patients. Moreover, these complications have detrimental effects on society in general. As one example, the global prevalence of diabetes mellitus afflicts millions of individuals resulting in significant increases of morbidity and mortality rates. These increased morbidity and mortality rates, together with the great financial burden of treating diabetic complications, are major incentives to search for and develop medications having the potential of preventing or treating complications of the disease.

The compounds of the present invention inhibit the nonenzymatic formation of glycation and dehydration condensation complexes known as advanced glycation end-products (AGE). In one embodiment of the present invention, a method is provided for administering a medication that inhibits the nonenzymatic formation of glycation and dehydration condensation complexes known as advanced glycation end-products (AGE) to a subject in need thereof, comprising providing at least one medication that inhibits the nonenzymatic formation of AGE complexes; and administering the medication to an patient wherein the nonenzymatic formation of AGE complexes is inhibited.

In another embodiment of the method, the administering step comprises a route of administration selected from the group consisting of oral, sublingual, intravenous, intracardiac, intraspinal, intraosseous, intraarticular, intrasynovial, intracutaneous, subcutaneous, intramuscular, epicutaneous, transdermal, conjunctival, intraocular, intranasal, aural, intrarespiratory, rectal, vaginal and urethral. In another embodiment, the administering step comprises providing the medication on an implantable medical device.

While these medications are typically parameter specific medications, they are efficacious in wound healing, in scar reduction and in the treatment of burns. For example, a compound that inhibits the formation of AGE complexes may be directly applied to in a conventional hydrophilic or oleophilic ointment base, or incorporated within, a medical device (i.e., a wound dressing, patch, etc.) and applied to a patient's skin to aid the wound healing process. MMP9 has been identified in the wound healing process and has also been linked to the inhibitors of AGE Any method of administering the medication(s) discussed herein is contemplated. While it is understood by one skilled in the art that the method of administration may depend on patient specific factors, the methods of administration include, but are not limited to, generally parenteral and nonparenteral administration. More specifically, the routes of administration include, but are not limited to oral, sublingual, intravenous, intracardiac, intraspinal, intraosseous, intraarticular, intrasynovial, intracutaneous, subcutaneous, intramuscular, epicutaneous, transdermal, conjunctival, intraocular, intranasal, aural, intrarespiratory, rectal, vaginal, urethral, etc. Typically, an oral route of administration is preferred.

Of course, it is understood that the medication will be administered in the appropriate pharmaceutical dosage, depending on the route of administration. For example, an oral dosage form may be administered in at least one of the following pharmaceutical dosage forms: tablet; capsule; solution; syrup; elixir; suspension; magma; gel; and/or powder. A sublingual preparation may be administered in at least one of the following pharmaceutical dosage forms: tablet; troche; and/or lozenge. A parenteral dosage form may be administered in at least one of the following pharmaceutical dosage forms: solution and/or suspension. An epicutaneous/transdermal dosage form may be administered in at least one of the following pharmaceutical dosage forms: ointment; cream; infusion pump; paste; plaster; powder; aerosol; lotion; transdermal patch/disc/solution. A conjunctival dosage form may be administered in at least one of the following pharmaceutical dosage forms: contact lens insert and/or ointment. An intraocular/intraaural dosage form may be administered in at least one of the following pharmaceutical dosage forms: solution and/or suspension. An intranasal dosage form may be administered in at least one of the following pharmaceutical dosage forms: solution; spray; inhalant and/or ointment. An intrarespiratory dosage form may be administered in at least one of the following pharmaceutical dosage forms: aerosol and/or powder. A rectal dosage form may be administered in at least one of the following pharmaceutical dosage forms: solution; ointment and/or suppository. A vaginal dosage form may be administered in at least one of the following pharmaceutical dosage forms: solution; ointment; emulsion foam; tablet; insert/suppository/sponge. A urethral dosage form may be administered in at least one of the following pharmaceutical dosage forms: solution and/or suppository.

The above-noted dosage form(s) may include at least one medication disclosed herein, either alone or in combination with at least one other medication disclosed herein or with a medication not disclosed herein and/or in combination with at least one inert pharmaceutical excipient. These medications may have any release profile including, but not limited to, an immediate release, a controlled release and/or a delayed release profile. If desired, the compounds of the invention may be applied as nanoparticles.

The medical devices include, but are not limited to, implantable medical devices such as, but not limited to, stents (both vascular and urethral), deposition implants (implantable medication releasing device), and/or a medication delivery pumps. Also, contemplated herein are topically applied medical devices including, but not limited to, patches, gauze, wraps, appliques, dressings, coverings, etc. In the case of a medical device, at least one medication may be releasably applied either to at least a portion of the surface of the device, or to a material applied to the surface of a device. Alternatively, at least one medication may be absorbed and/or adsorbed into or onto the device material so long as the medication may be released from the material at a later time.

The medication may be releasably applied to the medical device via any industrially acceptable method, including, but not limited to, spray coating, a waterfall method, heat annealing, etc., however, spray coating is typically preferred. Alternatively, the medical device may include at least one medication, wherein the medication is absorbed and/or adsorbed into or onto the medical device. This may be done by any industrially acceptable method. Also, it is contemplated herein that a medical device may include both at least one medication releasably applied to the medical device itself and/or a coating applied to the device and at least one medication absorbed and/or adsorbed into or onto the medical device itself.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

In the course of screening different classes of organic compounds for investigation of their possible inhibitory effects on advanced glycation endproducts (AGEs), it has been found that most of the phenylureido substituted phenoxy propionic acid derivatives tested have inhibitory effects and several of these compounds were potent inhibitors of AGE-formation at concentrations much lower than an equally inhibiting concentration of aminoguanidine.

The mechanism by which this class of compounds inhibits glycation, AGE-formation, and crosslinking is yet to be known in full. Two major mechanisms, transient-metal-chelation such as copper and iron, and scavenging or trapping of reactive carboynyl intermediates have been proposed to be responsible for AGE-inhibitory function of known AGE-inhibitors.

The mechanism of the inhibitory activities of guanidino compound inhibitors such as two known inhibitors of glycation (aminoguanidine and metformin) is that they are postulated to trap MG and other alpha.-dicarbonyl intermediates of glycation. A most recent study has documented the reaction of metformin with MG and glyoxal (GO), forming guanidino-dicarbonyl adducts further supporting this idea (Ruggiero-Lopez et al., 1999).

Using known assay methods specific for the early (Amadori) and late (post-Amadori) stages of glycation revealed some inhibitors to have greater effects in the early stage and some in the late stage of glycation. However, most of the inhibitor compounds we have investigated are multistage inhibitors. The reaction of reducing sugars with .alpha.- and .epsilon.-amino groups of proteins is not a random process but rather a site specific reaction which depends on the nature and the vicinity of these chemical groups. The future task is to specifically define the site and/or sites of interaction of an inhibitor compound in the complex series of reactions and intermediate substrates; leading to AGE formation and cross-linking.

The development of the novel inhibitors of glycation, AGE formation, and AGE-protein crosslinking expands the existing arsenals of inhibitors of glycation reaction that can find therapeutic applications for the prevention of diabetic complications, as well as the prevention of other diseases associated with increased glycation of proteins or lipids. Furthermore, the availability of these compounds may prove useful as tools to study the cascade of reactions and intermediate substrate in the process of AGE-formation and AGE-protein cross-linking.

The compounds of the invention and their useful compositions utilized in the present invention contain agents capable of reacting with the highly active carbonyl intermediate of an early glycation product thereby preventing those early products from later forming the advanced glycation endproducts or in the alternative as agents for "breaking" or reversing the AGE complexes after they form protein crosslinked compounds which cause protein aging. Doses of 1-2000 mg per day may be used to prevent the formation of AGE complexes or to break AGE complexes depending on the desired effect and the observed response in a patient. The formation of AGE has been linked to several pathologies which may be treated according to the invention including chronic inflammation, neuropathy, atherosclerosis, retinopathy, Alzheimer's disease, erectile dysfunction and diabetes. The compounds of the invention are useful for the treatment of pre-diabetes, Type I and Type II diabetes as well as the prevention and/or treatment of diabetic syndrome or diabetic complications such as elevated lipid levels, elevated cholesterol, retinopathy, kidney damage, circulatory disorders, neuropathy and the like. The compounds of the invention may be used as glycation breakers systemically or topically to reverse glycation and its effects such as facial wrinkles. The compounds of the invention also have activity against rheumatoid arthritis, Wilson's disease, atherosclerosis, neurodegenerative diseases such as Parkinson's or Alzheimer's, multiple sclerosis, neurotoxinemia, neurotoxins and metabolic syndrome. An oral dose for these conditions is preferred but other routes of administration may be utilized. An effective amount of an oral dose will be from 1-2000 mg daily preferable given in divided doses. It is presently contemplated that a dose of 250-500 mg daily would be preferred.

Other utilities envisioned for the present invention are prevention and treatment of aging of the skin by exerting an anti-aging effect that reduces wrinkles and makes the skin smoother. The compounds may be used as solutions or dispersions in water or a cream at a concentration of 0.1 to 10% by weight and used as a cosmetic on the skin to improve the smoothness, texture, appearance by preventing or treating aging of the skin. A particular use is the application of compounds to skin for the purpose of increasing the collagen content which will inhibit or reverse environmental aging effects. The compounds of the invention reduce the amount of MMP9 in the skin which is linked to wound healing and skin repair. Thus, they may be used systemically or topically for scleroderma, acne, psoriasis, inflammation, antioxidant effects or for chelation of metals. They may also be used post laser cosmetic treatment for skin rejuvenation to enhance skin healing and repair post treatment. For topical use, the compounds may be added to hydrophilic or oleophilic cosmetic bases in amounts of 0.01 to 10% by weight, and preferably 1-5% or they may be applied as a solution, a cream, a dispersion or a gel. For systemic use, the compounds may be administered orally at a dose of 1-2000 mg daily in divided doses. The dose will be adjusted depending on the observed effect using conventional dosing techniques. The compounds also inhibit spoilage of proteins in foodstuffs such as the browning reaction seen in certain fruits. The present agents are also useful in the area of oral hygiene as they prevent discoloration of teeth.

The compounds of the invention also have PPAR activity which is an acronym for peroxisome proliferator activated receptor which are a group of receptor isoforms which exist across biology. They are intimately connected to cellular metabolism (carbohydrate, lipid and protein) and cell differentiation. They are also transcript factors. Several types of PPARs have been identified: alpha, gamma 1, 2 and 3 as well as delta or beta. The alpha form is expressed in liver, kidney, heart, adipose tissues as well as in other tissues. The gamma 1 form is expressed in virtually all tissues including heart, muscle, colon, kidney, pancreas and spleen tissues. The gamma 2 form is expressed mainly in adipose tissue (30 amino acids or longer while gamma 3 is expressed in macrophage, large intestine and white adipose tissue. Delta is expressed in many tissues but mainly in brain, adipose tissue and skin. PPARs dimerize with the retinoid receptor and bind to specific regions on the DNA of the largest genes and when PPAR binds to its ligand, transcription of target genes is increased or decreased depending on the gene. The PPAR activity of the compounds of the invention is a property that confirms that the compounds of the invention are useful as antidiabetic compounds in the manner that the PPAR active compound pioglitazone is useful when administered orally to diabetics. The dose may be from 1 to 2000 mg orally and preferably 250-500 mg orally, daily basis given in divided doses.

To aid in the administration, the compound may be combined with a pharmaceutical acceptable diluent or carrier to form a pharmaceutical dosage form. The dosage form can be a liquid, solid, gel for immediate release or controlled release. Common pharmaceutical diluents or carriers are described in the Handbook of Pharmaceutical Excipients, $4^{th}$ addition, the United States Pharmacopiea, and Remington's Pharmaceutical Science.

An intermediate compound exo-3,6-epoxy-1,2,3,6-tetrahydrophthalic anhydride is prepared by reacting equimolar quantities of maleic anhydride and furan in THF as a crystalline compound from acetone, MO=125° C.(dic) This anhydride is treated with 1 equivalent of hydroxylamine hydrochloride and one mole of sodium carbonate dissolved in 250 ml water at 50-60° C. for one hour. The solid is recrystallized in acetone or alcohol to give shining white flakes (HONE), MP207° C. This compound is useful in the synthesis of peptides as it reacts with dicyclohexylcarbodiimide (DCCI) in non aqueous solution to make active esters of amino acids This intermediate makes it possible to obtain small non-racemized peptides in high yields by a further reaction with a second amino acid.

Compounds of the present invention can be prepared as follows:

EXAMPLE 1

Compound 1

3,3'-dichloro-1,1'-diphenyl-4,4'-diureidophenoxy-isobutyric acid

A mixture of 1.95 g (0.01 mole) of 4-aminophenoxyisobutyric acid and 3,3'-dichloro-1,1'-diphenyl-4,4'-diisocyante in 30 ml of cooled tetrahydrofuran (THF) and 0.4 g of NaOH are combined and stirred at room temperature for 24 hours. The THF is evaporated by blowing air. Excess water is added and to the resulting brown solution, about 1.0 g of dithionite is added and the precipitate is separated by filtration (slow) and washed twice with hot water. The filtrate is acidified with concentrated acetic acid and filtered The white powdery material is washed with cold water and dried with dithionite, filtered and acidified with acetic acid The white precipitate is filtered and dried giving 1.6 g (dry) yield 43%. The structure is set forth as structure 1. $C_{34}H_{32}Cl_2N_4O_8$; mw 695

EXAMPLE 2

Compound 2

Quinoline-2-(methyleneaminophenoxyisobutyric) acid

A mixture of 1.95 g (0.01 mole) of 4-aminoiphenoxyisobutyric acid, 2.28 g (0.01 mole) of 2-chloromethylquinoline hydrochloride; 3 g of potassium carbonate, 40 ml of water and 29 ml of isopropanol is refluxed and stirred for 24 hours and a dark brown solution with about 1 g of product is obtained. The product is worked up by adding sodium carbonate. Dithionite is added and the mixture is acidified with acetic acid and a brown powder is obtained. The structure is set forth as structure 2. $C_{20}H_{20}N_2O_3$; mw 336

EXAMPLE 3

Compound 3

2,3,4,5,6-(pentamethylbenzyl-4-aminophenoxy-isobutyric) acid

A mixture of 1.25 g (0.005 mole) of 3,6-bis(chloromethyl amine); 1.9 g. (0.01 mole) 4-aminophenoxyisobutyric acid, 2.0 g (0.01 mole) potassium carbonate and 25 ml of a 50:50 mixture of water and isopropanol is stirred for 24 hours. The mixture is treated as in Example 1 giving a solid with a melting point of 178-184° C. The structure is shown as structure 3 $C_{22}H_{29}N_1O_3$; mw 455

EXAMPLE 4

Compound 4

1-(4-cinnamylamino phenoxyisobutyric) acid

A mixture of 2.1 g (0.01 mole) of cinnamyl chloride; 2.0 g (about 0.02 mole) 4-aminophenoxyisobutyric acid, 2.1 g (about 0.015 mole) of potassium carbonate and 30 ml of water is heated and stirred overnight. A brownish solution is obtained and the solvent is evaporated to give a brownish gum. Water was added with acetic acid and a precipitate is obtained. After refrigeration, the material is filtered, washed and dried. The structure is set forth as structure 4. $C_{19}H_{21}N_1O_6$; mw 317

EXAMPLE 5

Compound 5

4-(1-carboxy-3-carboxylamidophenoxyisobutyric) acid 3.1 g (0.02 mole) of the mono(active ester) of HONE ester of glutaric acid ($C_{13}H_{13}NO_6$) is mixed with 2.0 g (0.01 mole) of 4-amino isobutyric acid and 3.0 g (0.30 mole) of potassium carbonate in 30 ml of water. The reaction mixture is stirred and heated at 100° C. overnight and a brown paste is recovered and dissolved in hot water. Dithionite is added to partially clarify the material which is acidified with acetic acid which yields 1.40 g of a beige precipitate. The structure is structure 5 $C_{15}H_{19}N_1O_6$; mw 309

EXAMPLE 6

Compound 6

1,6-(4-carbobutoxyphenyl)hexane-4,4'-dioxyisobu-tyric) acid

A mixture of 3.9 g (0.02) of 4-amino phenoxyisobutyric acid, 1.8 ml (0.01 mole) of 1,6-diisocyanate hexane, 1.00 g (0.02 mole) sodium hydroxide 35 ml of THF and 5 ml of water is stirred and warmed to 40-45° C. overnight for 24 hours. After the THF is evaporated, about 50 ml of water is added and about 2 g of sodium carbonate is added and dithionite is added and the material is acidified with acetic acid. The product is filtered, washed with water and dried yielding an off white powder (about 2.45 g) mp 198° C. (dec.) The structure is structure 6. $C_{28}H_{38}N_4O_8$; mw 556

EXAMPLE 7

Compound 7

2,2'-(((((cyclohexane-1,4-diylbis(azanediyl))bis(carbonyl))bisazanediyl))bis(4,1-phenylene))bis(oxy)bis (2-methylpropanoic acid)

A mixture of 1.72 g (0.01 mole) of trans 1,4-cyclohexane diisocyanate, 3.0 g (0.01 mole) of 4-amino phenoxyisobutyric acid, 1.0 g (0.20 mole) of sodium hydroxide, 5 ml of water and 35 ml of THF is stirred and refluxed overnight. After working up the reaction product 1.58 g of material is obtained The material is light sensitive and turns to a purple powder by exposure to daylight. The product has a melting point of 230°. The structure is structure 7. $C_{28}H_{38}N_4O_8$; mw 556

EXAMPLE 8

Compound 8

2,2-dichlorobenzoylamidophenoxyisobutyric acid

A mixture of 1.77 g (0.05 mole) of 2,3-dichlorobenzoicacid HONE ester; 1.95 g (0.05 mole) of 4-aminophenoxyisobutyric aid; 1.58 g (0.15 mole) of potassium carbonate and 30 ml of water are stirred and boiled overnight. More water is added and boiling is continued for six hours and the reaction mixture is filtered and treated with dithionite and acidified with acetic acid to give a white solid. A brown paste is obtained that is dissolved in hot water. Dithionite is added to partially clarify the mixture before acidification with acetic acid to give a beige precipitate. Yield is 1.45 g. The structure is set forth as structure 8. $C_{17}H_{15}Cl_2N_1O_3$; mw 547

EXAMPLE 9

Compound 9

1,2-diacetylamidoisobutyric acid

A mixture of 0.875 ml (5 mmoles) of 1,2-dichlorobenzoyl chloride; 1.95 g (10 mmoles) of 4-aminophenoxyisobutyric acid; 3.58 g (20 mmoles) of potassium carbonate in 20 ml of ethanol are stirred and refluxed for 24 hours. 20 ml of water us added and evaporated to remove ethanol. Dithionite is added, the mixture is filtered and acidifies with acetic acid to give a 50% yield of a white solid. MP about 220° C. (dec). The structure is structure 9. $C_{30}H_{32}N_2O_8$; mw 548

EXAMPLE 10

Compound 10

N-succinylamidophenoxyisobutyric acid

A mixture of 1.0 g (0.01 mole) of succinic anhydride; 1.95 g). 01 mole) of 4-aminophenoxyisobutyric acid; in 10 ml of water is stirred and boiled for 24 hours. A clear solution is obtained that is evaporated to yield a semi-solid gum. 20 ml of water is added and the mixture is gently heated to evaporate the water and yield an off white solid. The structure is structure 10. $C_{13}H_{17}N_1O_5$; mw 295

EXAMPLE 11

Compound 11

1,4-bis-phenyluridophenoxyisobutyric acid

A mixture of 3.9 g (0.02 mole) 4-aminophenoxyisobutyric acid, 0.8 g (0.02 mole) sodium hydroxide, 6 ml water and 60 ml tetrahydrofuren is cooled in a freezer before adding 3.5 g (0.02 mole) 4-bis-phenyoxyisocyanate with stirring. The mixture is then stirred at room temperature overnight. Finally the mixture is heated gently and air blown to evaporate before 6 ml 5N sodium hydroxide is added and left overnight stirring. Also water was added and gently warmed before filtration. Acidified with HCL to get precipitate. Practically 2 m 5N sodium hydroxide is added. The structure is shown as structure 11. $C_{28}H_{30}N_4O_5$ mw550

EXAMPLE 12

Compound 12

Oxo-bis-1,4-benzamidophenoxyisobutyric acid

A mixture of 5.26 g (0.02 mole) 4-oxy-bis-benzoic acid and 25 ml THF and 2.2 ml (0.02 mole) triethylamine is cooled in freezer and then 2.75 ml (0.02 mole) t-butylchloroformate is added while stirring. The product is cooled again in a freezer and 3.9 g (0.04 mole) 4-aminoisobutyric acid and 1 g sodium hydroxide in 5 ml cold water is added with 20 ml THF and the solution is stirred for 2 hours. It is then evaporated by blowing air becoming a thick syrup. Cold water is added and evaporated to remove the rest of the THF. It is then acidified with acetic acid and 1 g dithionite added. The white precipitate is cooled and filtered. It is washed with water and left at room temperature to dry. The product is a white solid. To recrystallize a sample of 250 mg is dissolved in 10 ml isopropanol diluted with water and refrigerated to recrystallize into a granular white powder which is dried at room temperature for one week . . . . Total yield 6.35 g (about 100%). The structure is structure 12. $C_{34}H_{32}N_2O_9$; mw 610; mp 212-215° C.

EXAMPLE 13

Compound 13

2,6 dinaphtoxybenzamido-4,4'-phenoxyisobutyric acid

A mixture of 2.225 g (0.01 mole) 2-6 naphthalenedicarboxysilic acid, 25 ml tetrahydrofuran (THF) and 2.2 ml (0.02 mole) triethylamine is cooled in a freezer and then 2.75 ml (0.02 mole) benzylchoroformate is added with stirring. This ice cooled product is added to 3.9 g 4-aminophenoxyisobutyric acid and dissolved in a solution of 1 g sodium hydroxide in 5 ml water cooled. The mixture is stirred at room temperature and then evaporated at room temperature (air) to remove THF. It is then acidified with acetic acid and 2.2 g of starting dicarboxylic acid as white powder is recovered. The structure is structure 13. $C_{32}H_{30}N_2O_8$ mw 570 mp greater than 300° C. The above compound is also made using ethylchoroformate instead of benzylchloroformate giving 60% yield.

EXAMPLE 14

Compound 14

Quinoline-4-carboxamido-4-phenoxyisobutyric acid

A mixture of 1 g (0.03 mole) HONE ester and 0.6 g (0.03 mole) 4-aminophenoxyisobutyric acid and 1 g (excess) potassium carbonate and 20 ml water was stirred and heated for 24 hours. It was evaporated to dryness and dissolved in 20 ml boiling water and filtered and acidified with citric acid and acetic acid. It was cooled and precipitate then filtered. The structure is structure 14. $C_{20}H_{18}N_2O_4$ mw370

EXAMPLE 15

Compound 15

2-phenylquinolyl-4-carboxamidophenoxyisobutyric acid

A mixture 011.42 g (0.05 mole) HONE ester of 2-phenylquinoline-4-carboxylic acid and 0.975 g 0.05 mole) 4-aminophenoxyisobutyric acid and 1.38 g (0.10 mole) of potassium carbonate is added to 25 ml water and is stirred and refluxed for 24 hrs. After filtration, it is acidified to give the desired compound. The structure is structure 15. $C_{26}H_{21}N_2O_4$ mw 425 mp198(dec)

EXAMPLE 16

Compound 16

4-(1,3,5-triphenoxyisobutylamidophenoxyisobutyric acid

A mixture of 0.085 g (0.0033 mole) 1,3,5-triphenoxyisobutyrlchloride and 1.95 g (0.01 mole) 4-aminophenoxyisobutyric acid in 25 ml pyridine was refluxed for 48 hrs. Then 250 ml water was added and acidified with hydrochloric acid. A light brown product was obtained, filtered and washed with water and dried. The structure is structure 16. $C_{40}H_{33}N_3O_{12}$ mw 747 mp 235° C. (dec)

EXAMPLE 17

Compound 17

4-adamatoylamidophenoxyisobutyric acid

A mixture of 3.58 g (0.02 mole) 4-adamantylcarboxysylic acid is dissolved in 50 ml THF and 2 ml tritheylamine and is then cooled in ice bath and stirred for one half hour to get mixed anhydride. To the resulting product 3.9 g (0.02 mole) 4-aminophenoxyisobutyric acid is added and the stirring continued for 3 hrs. At this time the reaction product is filtered and evaporated to remove most of THF. An excess of sodium bicarbonate solution and charcoal powder is added to discolor the product. The product is acidified with hydrochloric acid and cooled and then filtered. The structure is structure 17. $C_{22}H_{25}N_1O_4$, mw 367 Any other carboxysylic acid could be used instead of adamantylcarboxsylic acid to obtain the carboxamido derivative. The structure is structure

EXAMPLE 18

Compound 18

4-cycloalkylquinolylcarboxamidophenoxisobutyric acid

A mixture of 2.94 g (0.02 mole) isatine and 50 ml ethanol and 2.24 g (0.04 mole) potassium hydroxide and 2 g (0.02 mole) cyclohexanone is refluxed to give cyclohexylquinoline-4-carboxylic acid. This acid is dried and dissolved in 50 ml THF and 2 ml ethylchloroformate and 2 ml three ethylamine are added over an ice bath. After 3 hrs stirring 3.9 g (0.02 mole) 4-aminophenoxyisobutyric acid is added and stirring continued for 4 hrs. After filtration most of THF is evaporated and diluted with water and acidified with hydrochloric acid to get the final compound. The structure is structure 18. $C_{29}H_{20}N_2O_4$ mw 400 If other cyclic ketones such as cycloheptanone are used the corresponding cycloheptyl compound is obtained.

EXAMPLE 19

Compound 19

4-piperonylcarboxamindophenoxyisobutyric acid

A mixture of 1.7 g (0.01 mole) piperonylic acid and 1 ml ethylchloroformate and 1 ml triethyllamine in 25 ml of dry acetone is stirred and cooled and at the end of about 1 hour, 1.95 gm (0.01 mole) 4-aminophenoisobutyric acid is added followed by the addition oft ml 1 N sodium hydroxide. Stirring continued at room temperature for 3 hours. The reaction product is filtered and most of the acetone is evaporated. 30 ml water is added and acidified with hydrogen chloride to precipitate. The solid is filtered, washed with water and air dried. The structure is structure 19. $C_{19}H_{19}N_1O_5$ mw 340

Compound No. 1 was tested for glycation activity according to the following protocol:

BSA was incubated in the presence of glucose and Compound No. 1 at 37° C. for 5 weeks. Aliquots of 2 μg protein were run on an SDS gel and transferred to PVDF membrane—the same procedure as for a western blot. The membrane was then processed to identify glycoprotein content by the periodic acid-Schiff base method. The positive reaction is pink, and glycation also shifts the molecular weight so the band migrates more slowly down the gel (higher position on the blot). BSA alone shows faint staining—and about 5% of this protein is glycated normally. Amimoguanadine was used as a control Reduced staining is an indication of glycation inhibition.

Compound No. 1 was found to inhibit glycation.

The compounds of the invention may be used in veterinary medicine for those conditions described herein which occur in domestic animals, such as dogs and cats as well as in larger animals such as horses and farm animals including cattle, pigs sheep and the like.

We claim:

1. A compound of the formula:

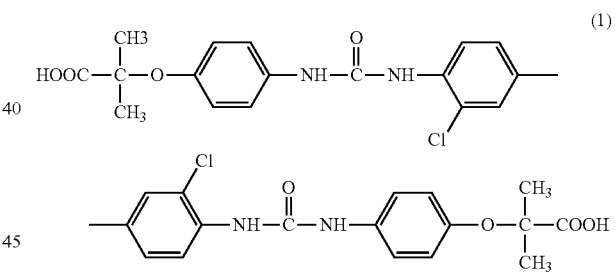

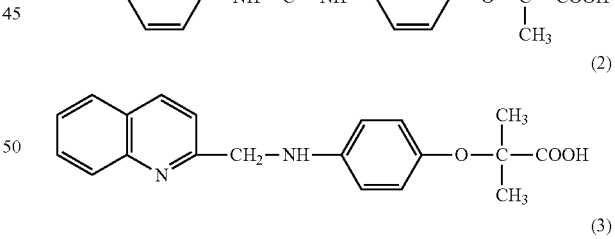

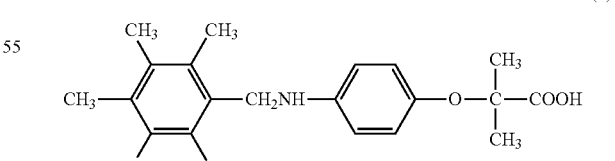

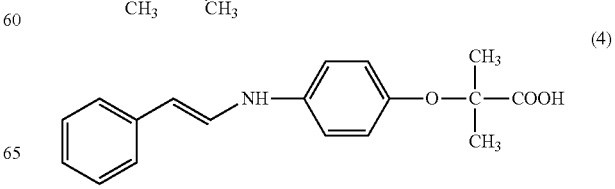

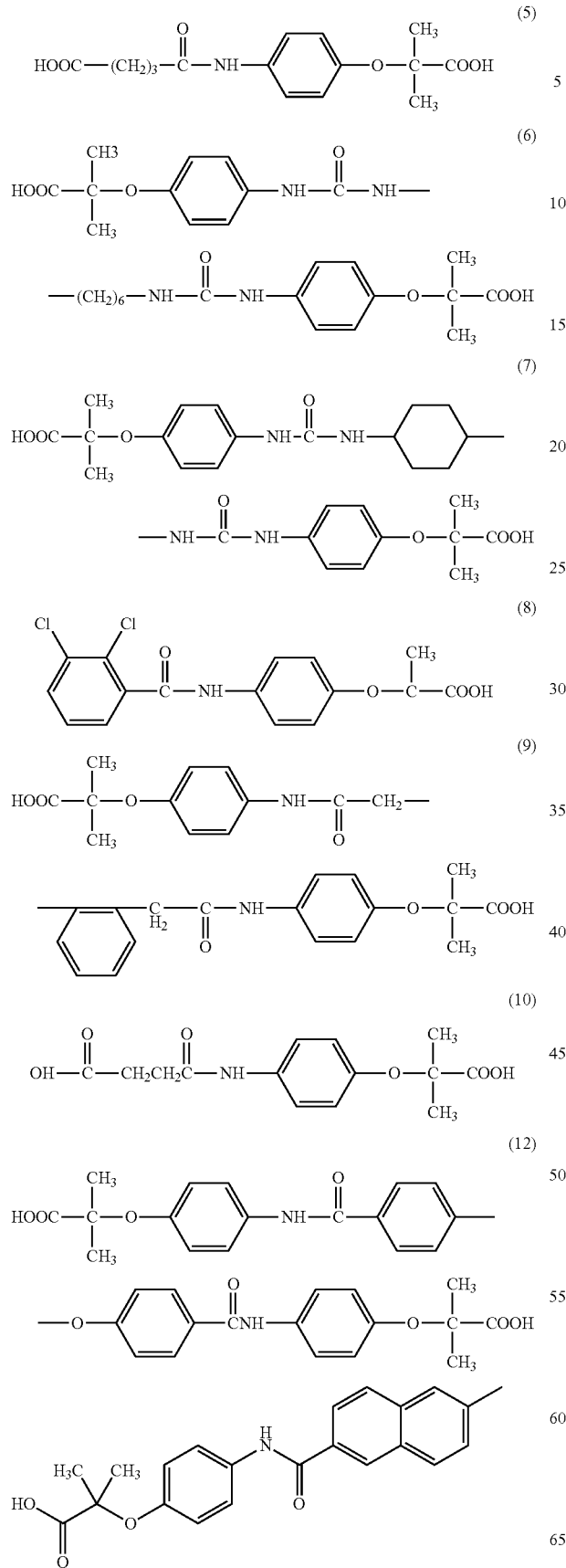
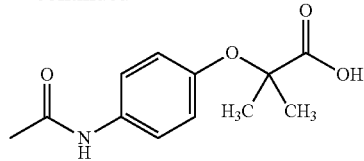
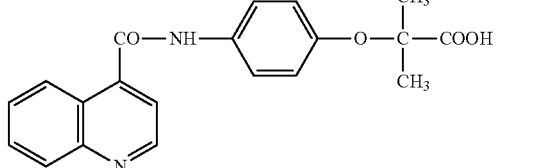
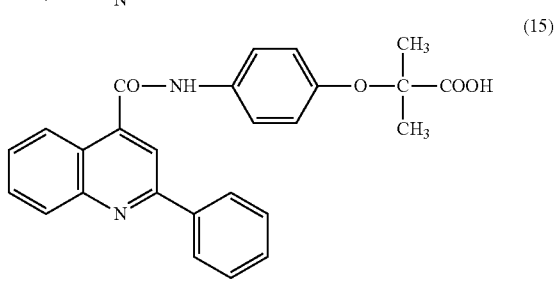
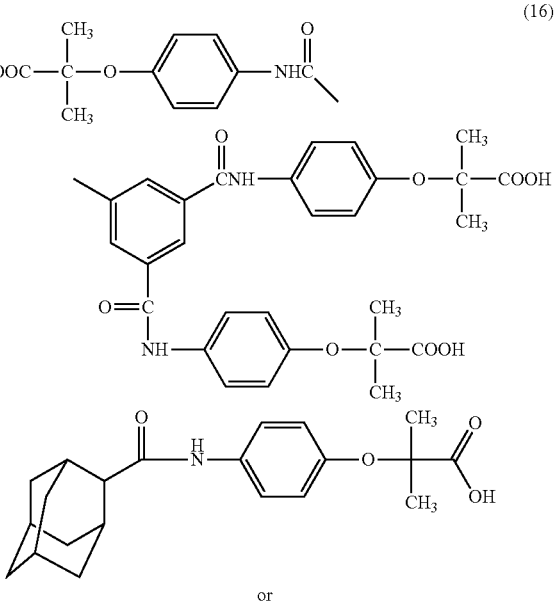
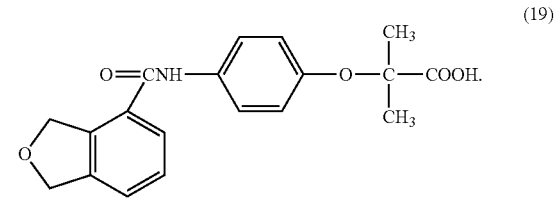

2. A pharmaceutical composition which comprises a compound as defined in claim 1 and a pharmaceutically acceptable diluent.

3. A pharmaceutically acceptable salt of a compound of claim 1 and a pharmaceutical carrier.

4. A method of treating Type I diabetes which comprises administering to a Type I diabetic patient an effective amount of a compound of claim 1 or a pharmaceutically acceptable salt of said compound.

5. A method of treating Type II diabetes which comprises administering to a Type II diabetic patient an effective amount of a compound of claim 1 or a pharmaceutically acceptable salt of said compound.

\* \* \* \* \*